United States Patent
Charrier et al.

(10) Patent No.: US 10,098,825 B2
(45) Date of Patent: *Oct. 16, 2018

(54) DYE COMPOSITION COMPRISING A PARTICULAR AMPHOTERIC SURFACTANT AND AN OXYETHYLENATED AMIDE SURFACTANT OR AN OXYETHYLATENATED FATTY ALCOHOL SURFACTANT COMPRISING LESS THAN 10 OE UNITS AND MIXTURE THEREOF

(71) Applicant: L'OREAL, Paris (FR)

(72) Inventors: Delphine Charrier, Boulogne Billancourt (FR); Aurélie Camblong, Courbevoie (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/905,574

(22) PCT Filed: Jul. 21, 2014

(86) PCT No.: PCT/EP2014/065632
§ 371 (c)(1),
(2) Date: Jan. 15, 2016

(87) PCT Pub. No.: WO2015/007915
PCT Pub. Date: Jan. 22, 2015

(65) Prior Publication Data
US 2016/0151264 A1    Jun. 2, 2016

(30) Foreign Application Priority Data

Jul. 19, 2013 (FR) ..................... 13 57120
Jul. 19, 2013 (FR) ..................... 13 57125

(51) Int. Cl.
*A61Q 5/10* (2006.01)
*A61K 8/41* (2006.01)
(Continued)

(52) U.S. Cl.
CPC ............... *A61K 8/411* (2013.01); *A61K 8/31* (2013.01); *A61K 8/342* (2013.01); *A61K 8/345* (2013.01);
(Continued)

(58) Field of Classification Search
CPC . A61Q 5/10; A61K 8/31; A61K 8/345; A61K 8/442; A61K 8/45; A61K 8/415;
(Continued)

(56) References Cited

U.S. PATENT DOCUMENTS 3,589,978 A    6/1971 Kamal et al.
3,792,068 A    2/1974 Luedders et al.
(Continued)

FOREIGN PATENT DOCUMENTS

CN    1474682 A    2/2004
CN    101411676 A    4/2009
(Continued)

OTHER PUBLICATIONS

STIC Search Report dated Mar. 30, 2016.*
International Search Report for PCT/EP2014/065633, dated Oct. 7, 2014.
International Search Report for PCT/EP2014/065632, dated Oct. 6, 2014.
International Search Report for PCT/EP2014/065635, dated Sep. 22, 2014.
Porter, M.R., "Handbook of Surfactants," published by Blackie & Son (Glasgow and London), 1991, pp. 116-178.
Morishima, Yotaro, "Self-Assembling Amphiphilic Polyelectrolytes and their Nanostructures," Chinese Journal of Polymer Science, vol. 18, No. 40, (2000), pp. 323-336.
Noda, Tetsuya, et al., "Micelle Formation of Random Copolymers of Sodium 2-(Acrylamide)-2-Methylpropanesulphonate and a Nonionic Surfactant Macromonomer in Water as Studied by Fluorescence and Dynamic Light Scattering," Macromolecules 2000, 33, pp. 3694-3704.
(Continued)

*Primary Examiner* — Eisa B Elhilo
(74) *Attorney, Agent, or Firm* — The Marbury Law Group, LLC

(57) ABSTRACT

The present invention relates to a composition for dyeing keratin fibers, comprising: a) one or more liquid fatty substances; b) one or more amphoteric surfactants of formula (I) below: $R_a$—C(O)—NH—CH$_2$—(CH$_2$)$_n$—N(B)(B'); in which: B represents the group —CH$_2$—CH$_2$—O—X'; B' represents the group —(CH$_2$)$_z$Y', with z=1 or 2; X' represents the group —CH$_2$—C(O)OH, —CH$_2$—C(O)OZ', —CH$_2$—CH$_2$—C(O)OH or —CH$_2$—CH$_2$—C(O)OZ', or a hydrogen atom; Y' represents the group —C(O)OH, —C(O)OZ", —CH$_2$—CH(OH)—SO$_3$H or the group —CH$_2$—CH(OH)—SO$_3$—Z"; Z' and Z" represent, independently of each other, a cationic counterion derived from an alkali metal or alkaline-earth metal, such as sodium, an ammonium ion or an ion derived from an organic amine; $R_{a'}$ represents a C$_{10}$-C$_{30}$ alkyl or alkenyl group derived from an acid $R_{a'}$—C(O)OH, which is preferably present in copra oil or in hydrolyzed linseed oil, an alkyl group, especially a C$_{17}$ group and its iso form, or an unsaturated C$_{17}$ group and n represents an integer ranging from 1 to 10 and preferably from 1 to 5, or quaternized forms thereof; c) one or more nonionic surfactants chosen from oxyethylenated amide, oxyethylenated (OE) fatty alcohol comprising less than 10 OE units and mixture thereof; d) one or more oxidation dye precursors and e) one or more chemical oxidizing agents. The present invention also relates to a process using this composition and to a multi-compartment device that is suitable for performing the said process.

18 Claims, No Drawings

(51) Int. Cl.
*A61K 8/31* (2006.01)
*A61K 8/34* (2006.01)
*A61K 8/44* (2006.01)
*A61K 8/45* (2006.01)
*A61K 8/81* (2006.01)
*B65D 81/32* (2006.01)

(52) U.S. Cl.
CPC .............. *A61K 8/415* (2013.01); *A61K 8/442* (2013.01); *A61K 8/45* (2013.01); *A61K 8/817* (2013.01); *A61Q 5/10* (2013.01); *B65D 81/32* (2013.01); *A61K 2800/4324* (2013.01); *A61K 2800/88* (2013.01)

(58) Field of Classification Search
CPC ........ A61K 8/411; A61K 8/342; A61K 8/817; A61K 2800/88; A61K 2800/4324; B65D 81/32
See application file for complete search history.

(56) References Cited

U.S. PATENT DOCUMENTS

| | | | |
|---|---|---|---|
| 4,003,699 | A | 1/1977 | Rose et al. |
| 4,017,460 | A | 4/1977 | Tessler |
| 4,031,307 | A | 6/1977 | DeMartino et al. |
| 4,137,180 | A | 1/1979 | Naik et al. |
| RE30,199 | E | 1/1980 | Rose et al. |
| 4,874,554 | A | 10/1989 | Lange et al. |
| 5,089,578 | A | 2/1992 | Valint et al. |
| 5,455,340 | A | 10/1995 | Bernard et al. |
| 6,284,003 | B1 | 9/2001 | Rose et al. |
| 6,645,476 | B1 | 11/2003 | Morschhauser et al. |
| 6,730,789 | B1 | 5/2004 | Birault et al. |
| 6,822,039 | B1 | 11/2004 | Monfreux-Gaillard et al. |
| 7,931,698 | B2 | 4/2011 | Simonet et al. |
| 2002/0010970 | A1* | 1/2002 | Cottard .................. A61K 8/342 8/405 |
| 2003/0074747 | A1* | 4/2003 | Vuarier .................... A61Q 5/10 8/405 |
| 2004/0091444 | A1 | 5/2004 | Loffler et al. |
| 2004/0096409 | A1 | 5/2004 | Loeffler et al. |
| 2004/0097657 | A1 | 5/2004 | Morschhauser et al. |
| 2004/0109835 | A1 | 6/2004 | Loffler et al. |
| 2004/0109836 | A1 | 6/2004 | Loffler et al. |
| 2004/0109838 | A1 | 6/2004 | Morschhauser et al. |
| 2004/0115148 | A1 | 6/2004 | Loffler et al. |
| 2004/0115149 | A1 | 6/2004 | Loffler et al. |
| 2004/0115157 | A1 | 6/2004 | Loffler et al. |
| 2004/0116628 | A1 | 6/2004 | Morschhauser et al. |
| 2004/0116634 | A1 | 6/2004 | Morschhauser et al. |
| 2004/0141930 | A1 | 7/2004 | Legrand |
| 2004/0141937 | A1 | 7/2004 | Loffler et al. |
| 2004/0167304 | A1 | 8/2004 | Morschhauser et al. |
| 2005/0002977 | A1 | 1/2005 | Mallo |
| 2005/0032998 | A1 | 2/2005 | Morschhauser et al. |
| 2005/0089536 | A1 | 4/2005 | Loffler et al. |
| 2005/0232887 | A1 | 10/2005 | Morschhauser et al. |
| 2008/0069793 | A1 | 3/2008 | Loffler et al. |
| 2008/0107617 | A1 | 5/2008 | Loffler et al. |
| 2008/0207773 | A1 | 8/2008 | Loffler et al. |
| 2010/0154140 | A1* | 6/2010 | Simonet .................. A61K 8/31 8/416 |
| 2014/0068876 | A1 | 3/2014 | Rapold et al. |

FOREIGN PATENT DOCUMENTS

| | | |
|---|---|---|
| CN | 101843561 A | 9/2010 |
| DE | 2359399 A1 | 6/1975 |
| DE | 19701422 C1 | 3/1998 |
| DE | 102005048606 A1 | 4/2007 |
| DE | 102007060530 A1 | 9/2009 |
| DE | 102008061676 A1 | 11/2009 |
| DE | 102008036535 A1 | 2/2010 |
| EP | 0750899 A2 | 1/1977 |
| EP | 0770375 A1 | 5/1997 |
| EP | 1069142 A1 | 1/2001 |
| EP | 1415641 A1 | 5/2004 |
| EP | 1600150 A1 | 11/2005 |
| EP | 2143414 A2 | 1/2010 |
| EP | 2143419 A2 | 1/2010 |
| EP | 2198846 A1 | 6/2010 |
| FR | 2801308 A1 | 5/2001 |
| FR | 2856691 A1 | 12/2004 |
| FR | 2893407 A1 | 5/2007 |
| FR | 2970176 A1 | 7/2012 |
| GB | 1026978 A | 4/1966 |
| GB | 1153196 A | 5/1969 |
| JP | 02-019576 A | 1/1990 |
| JP | 05-163124 A | 6/1993 |
| WO | 96/15765 A1 | 5/1996 |
| WO | 00/31154 A1 | 6/2000 |
| WO | 02/43689 A2 | 6/2002 |
| WO | 2006/136303 A1 | 12/2006 |
| WO | 2014/020147 A2 | 2/2014 |
| WO | 2014/020148 A1 | 2/2014 |
| WO | 2015/007916 A1 | 1/2015 |
| WO | 2015/007917 A1 | 1/2015 |

OTHER PUBLICATIONS

Noda, Tetsuya et al., "Solution Properties of Micelle Networks Formed by Nonionic Moieties Covalently Bound to a Polyelectrolyte: Salt Effects on Rheological Behavior," Langmuir 2000, 16, pp. 5324-5332.
Noda, Tetsuya, et al., "Stimuli-Responsive Amphiphilic Copolymers of Sodium 2-(Acrylamide)-2-Methylpropanesulphonate and Associative Macromonomers," Polym. Preprint, Div. Polym. Chem. 1999, 40(2), pp. 220-221.
Todd, Charles, et al., "Volatile Silicone Fluids for Cosmetic Formulations," Cosmetics and Toiletries, vol. 91, Jan. 1976, pp. 29-32.
English language abstract for DE 19701422 C1 (Mar. 5, 1998).
English language abstract for DE 102005048606 A1 (Apr. 19, 2007).
English language abstract for DE 102007060530 A1 (Sep. 17, 2009).
English language abstract for DE 102008036535 A1 (Feb. 11, 2010).
English language abstract for DE 102008061676 A1 (Nov. 19, 2009).
English language abstract for EP 0770375 A1 (May 2, 1997).
English language abstract for EP 2143414 A2 (Jan. 13, 2010).
English language abstract for EP 2143419 A2 (Jan. 13, 2010).
English language abstract for JP 02-019576 A (Jan. 23, 1990).
English language abstract for JP 05-163124 A (Jun. 29, 1993).
Non-Final Office Action for co-pending U.S. Appl. No. 14/905,586 (dated Dec. 29, 2016).
Non-Final Office Action for co-pending U.S. Appl. No. 14/905,554 (dated Dec. 30, 2016).
Mintel: "Men's Own Hair Colourant," XP-002722971, Sep. 2009.
First Office Action for counterpart Chinese Application No. 201480040294.9, dated Mar. 30, 2017.
Office Action for counterpart Chinese Application No. 201480040293.4, dated Apr. 5, 2017.
Final Office Action for co-pending U.S. Appl. No. 14/905,554, dated Jul. 21, 2017.
Final Office Action for co-pending U.S. Appl. No. 14/905,586, dated Jul. 21, 2017.
Office Action for counterpart Chinese Application No. 201480040293.4, dated Dec. 25, 2017.
Non-Final Office Action for co-pending U.S. Appl. No. 14/905,554, dated Jan. 11, 2018.
Notice of Allowance for co-pending U.S. Appl. No. 14/905,586, dated Feb. 26, 2018.

* cited by examiner

DYE COMPOSITION COMPRISING A PARTICULAR AMPHOTERIC SURFACTANT AND AN OXYETHYLENATED AMIDE SURFACTANT OR AN OXYETHYLATENATED FATTY ALCOHOL SURFACTANT COMPRISING LESS THAN 10 OE UNITS AND MIXTURE THEREOF

CROSS REFERENCE TO RELATED APPLICATION

This is a national stage application of PCT/EP2014/065632, filed internationally on Jul. 21, 2014, which claims priority to French Application Nos. 1357120 and 1357125, which were both filed on Jul. 19, 2013, all of which are incorporated herein by reference in their entireties.

The present invention relates to a composition for dyeing keratin fibres, comprising a liquid fatty substance, a particular amphoteric surfactant, a nonionic surfactant chosen from oxyethylenated amide and oxyethylenated (OE) fatty alcohol comprising less than 10 OE units, an oxidation dye and a chemical oxidizing agent such as hydrogen peroxide.

The present invention also relates to a dyeing process using this composition and to a multi-compartment device that is suitable for the use of this composition.

Many people have sought for a long time to modify the colour of their hair and in particular to mask their grey hair.

One of the dyeing methods is "permanent" or oxidation dyeing, which uses dye compositions containing oxidation dye precursors, generally known as oxidation bases. These oxidation bases are colourless or weakly coloured compounds which, in combination with oxidizing products, can give rise to coloured compounds by an oxidative condensation process.

Permanent dyeing processes thus consist in using, with the dye composition, an aqueous composition comprising at least one oxidizing agent, under alkaline pH conditions in the vast majority of cases. The role of this oxidizing agent is, at least in part, to degrade the melanin of the hair, which, depending on the nature of the oxidizing agent present, leads to more or less pronounced lightening of the fibres. The oxidizing agent used is generally hydrogen peroxide.

One of the difficulties encountered during the implementation of the dyeing processes of the prior art arises from the fact that they are carried out under alkaline conditions and that the basifying agents most commonly used are aqueous ammonia and amines. Specifically, the basifying agent makes it possible to adjust the pH of the composition to an alkaline pH to enable activation of the oxidizing agent. In addition, this basifying agent causes swelling of the keratin fibre, with raising of the scales, which promotes the penetration of the oxidizing agent, and also of the dyes, if they are present, essentially oxidation dyes, into the fibre, and thus increases the efficacy of the dyeing or lightening reaction.

However, these basifying agents, and especially aqueous ammonia, cause the user discomfort due to their strong characteristic odour.

Moreover, not only may the user be inconvenienced by the odour, but may also be confronted with greater risks of intolerance, for instance irritation of the scalp, which is especially reflected by stinging.

The oxidation dye must moreover satisfy a certain number of requirements. Thus, it must be free of toxicological drawbacks, it must enable shades to be obtained in the desired intensity and it must show good resistance to external attacking factors such as light, bad weather, washing, permanent waving, perspiration and rubbing.

The dyes must also be powerful and be able to cover grey hair and, finally, they must be as unselective as possible, i.e. they must produce the smallest possible colour differences along the same keratin fibre, which generally comprises areas that are differently sensitized (i.e. damaged) from its end to its root.

The compositions obtained must also have good mixing and application properties, and especially good rheological properties so as not to run down the face, onto the scalp or beyond the areas that it is proposed to dye, when they are applied.

Finally, the colorations must, as far as is possible, respect the integrity of the keratin fibres and give the said fibres the best possible cosmetic properties.

Many attempts have been made in the field of hair dyeing in order to improve the dyeing properties, for example using adjuvants. However, the choice of these adjuvants is difficult in so far as they must improve the dyeing properties of dye compositions without harming the other properties of these compositions. In particular, these adjuvants must not harm the stability of the compositions, the application properties of the coloration or the cosmetic properties of the dyed fibres.

One of the objects of the present invention is to propose compositions for dyeing human keratin fibres such as the hair that do not have the drawbacks of the existing compositions.

The compositions according to the invention have good working qualities on heads, and especially they are easy to use, do not run and allow uniform spreading on the hair.

They make it possible to obtain colours that are satisfactory, especially in terms of power in general, but also with satisfactory build-up of the colour at the root of the hair, which makes it possible to avoid a "root" effect of the coloration. The colorations obtained are also sparingly selective.

These aims and others are achieved by the present invention, one subject of which is thus a cosmetic composition for dyeing keratin fibres, in particular human keratin fibres such as the hair, comprising:

a) one or more liquid fatty substances;
b) one or more amphoteric surfactants of formula (I) below:

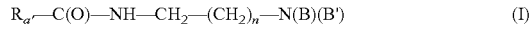

$$R_{a'}\text{—C(O)—NH—CH}_2\text{—(CH}_2)_n\text{—N(B)(B')} \quad (I)$$

in which:
 B represents the group —CH$_2$—CH$_2$—O—X';
 B' represents the group —(CH$_2$)$_z$Y', with z=1 or 2;
 X' represents the group —CH$_2$—C(O)OH, —CH$_2$—C(O)OZ', —CH$_2$—CH$_2$—C(O)OH or —CH$_2$—CH$_2$—C(O)OZ', or a hydrogen atom;
 Y' represents the group —C(O)OH, —C(O)OZ", —CH$_2$—CH(OH)—SO$_3$H or the group —CH$_2$—CH(OH)—SO$_3$—Z";
 Z' and Z" represent, independently of each other, a cationic counterion derived from an alkali metal or alkaline-earth metal, such as sodium, an ammonium ion or an ion derived from an organic amine;
 R$_{a'}$ represents a C$_{10}$-C$_{30}$ alkyl or alkenyl group derived from an acid R$_{a'}$—C(O)OH, which is preferably present in copra oil or in hydrolysed linseed oil, an alkyl group, especially a C$_{17}$ group and its iso form, or an unsaturated C$_{17}$ group and n represents an integer ranging from 1 to 10 and preferably from 1 to 5,
or quaternized forms thereof,
c) one or more nonionic surfactants chosen from oxyethylenated amide, oxyethylenated (OE) fatty alcohol comprising less than 10 OE units and mixture thereof;
d) one or more oxidation dye precursors and
e) one or more chemical oxidizing agents,
the composition comprising at least 10% by weight of liquid fatty substances, relative to the total weight of the composition.

A subject of the invention is also a dyeing process using the composition of the invention, and a multi-compartment device for using the composition of the invention.

Thus, the use of the dye composition according to the invention leads to powerful, intense, chromatic and/or sparingly selective colorations, i.e. colorations that are uniform along the fibre.

Furthermore, the processes according to the invention use formulations that are less malodorous during their application to the hair or during their preparation.

Other characteristics and advantages of the invention will emerge more clearly on reading the description and the examples that follow.

In the text hereinbelow, and unless otherwise indicated, the limits of a range of values are included within that range.

The human keratin fibres treated via the process according to the invention are preferably the hair.

The expression "at least one" is equivalent to the expression "one or more".

a) Liquid Fatty Substances

As has been mentioned, the composition of the invention comprises one or more fatty substances that are liquid at room temperature (25° C.) and at atmospheric pressure (760 mmHg or $1.013 \times 10^5$ Pa). These liquid fatty substances are generally referred to as oils.

The term "fatty substance" means an organic compound that is insoluble in water at ordinary temperature (25° C.) and at atmospheric pressure (760 mmHg or $1.013 \times 10^5$ Pa) (solubility of less than 5%, preferably of less than 1% and even more preferentially of less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention do not contain any salified carboxylic acid groups.

In particular, the fatty substances of the invention are not (poly)oxyalkylenated or (poly)glycerolated ethers.

The term "oil" means a "fatty substance" that is liquid at room temperature (25° C.) and at atmospheric pressure (760 mmHg or $1.013 \times 10^5$ Pa).

The term "non-silicone oil or fatty substance" means an oil or fatty substance not containing any silicon atoms (Si) and the term "silicone oil or fatty substance" means an oil or fatty substance containing at least one silicon atom.

More particularly, the fatty substances are chosen from $C_6$-$C_{16}$ liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid fatty acid and/or fatty alcohol esters other than triglycerides, and silicone oils, and mixtures thereof.

It is recalled that the fatty alcohols, esters and acids more particularly contain at least one saturated or unsaturated, linear or branched hydrocarbon-based group comprising 6 to 30 and better still from 8 to 30 carbon atoms, which is optionally substituted, in particular by one or more hydroxyl groups (in particular 1 to 4). If they are unsaturated, these compounds may comprise one to three conjugated or unconjugated carbon-carbon double bonds.

As regards the $C_6$-$C_{16}$ liquid hydrocarbons, they are linear, branched or optionally cyclic, and are preferably alkanes. Examples that may be mentioned include hexane, cyclohexane, undecane, dodecane, isododecane, tridecane or isoparaffins, such as isohexadecane or isodecane, and mixtures thereof.

The linear or branched hydrocarbons of mineral or synthetic origin comprising more than 16 carbon atoms are preferably chosen from liquid paraffins, petroleum jelly, liquid petroleum jelly, polydecenes and hydrogenated polyisobutene such as Parleam®, and mixtures thereof.

A hydrocarbon-based oil of animal origin that may be mentioned is perhydrosqualene.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil, and mixtures thereof.

As regards the fluoro oils, they may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The liquid fatty alcohols that are suitable for use in the invention are more particularly chosen from linear or branched, saturated or unsaturated alcohols comprising from 6 to 30 carbon atoms and preferably from 8 to 30 carbon atoms. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof.

As regards the liquid esters of fatty acids and/or of fatty alcohols other than the triglycerides mentioned above, mention may be made especially of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Preferably, for the esters of monoalcohols, at least one of the alcohol or of the acid from which the esters of the invention result is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononate; octyldodecyl erucate; oleyl erucate; ethyl palmitate, isopropyl palmitate, 2-ethylhexyl palmitate, 2-octyldecyl palmitate, alkyl myristates such as isopropyl 2-octyldodecyl myristate, isobutyl stearate; 2-hexyldecyl laurate, and mixtures thereof.

Preferably, among the monoesters of monoacids and of monoalcohols, use will be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose mono- or dioleates, stearates, behenates, oleopalmitates, linoleates, linolenates and oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

The silicones that may be used in the dye composition according to the present invention are volatile or non-volatile, cyclic, linear or branched silicones, which are unmodified or modified by organic groups, having a viscosity from $5 \times 10^{-6}$ to $2.5$ m$^2$/s at 25° C., and preferably $1 \times 10^{-5}$ to 1 m$^2$/s.

The silicones that may be used in accordance with the invention are in the form of oils.

Preferably, the silicone is chosen from polydialkylsiloxanes, especially polydimethylsiloxanes (PDMS), and liquid polyorganosiloxanes comprising at least one aryl group.

These silicones may also be organomodified. The organomodified silicones that may be used in accordance with the invention are liquid silicones as defined above and comprising in their structure one or more organofunctional groups attached via a hydrocarbon-based group, chosen, for example, from amine groups and alkoxy groups.

Organopolysiloxanes are defined in greater detail in Walter Noll's *Chemistry and Technology of Silicones* (1968), Academic Press. They may be volatile or nonvolatile.

When they are volatile, the silicones are more particularly chosen from those with a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold especially under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

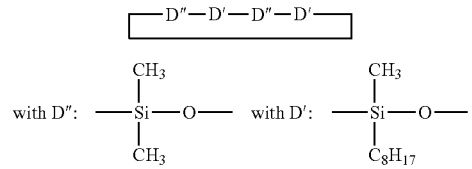

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold especially under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*.

Non-volatile polydialkylsiloxanes are preferably used.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm²/s;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

The organomodified silicones that may be used in accordance with the invention are silicones as defined previously and comprising in their structure one or more organofunctional groups attached via a hydrocarbon-based group.

As regards the liquid polyorganosiloxanes comprising at least one aryl group, they may especially be polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m²/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may be made of polyorganosiloxanes comprising:

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;
alkoxy groups.

Preferably, the liquid fatty substances according to the invention are non-silicone.

The liquid fatty substances are advantageously chosen from liquid $C_6$-$C_{16}$ alkanes, liquid hydrocarbons comprising more than 16 carbon atoms, plant oils of triglyceride type, liquid synthetic triglycerides, liquid fatty alcohols, liquid fatty acid and/or fatty alcohol esters other than triglycerides, and mixtures thereof.

Preferably, the liquid fatty substance is chosen from liquid petroleum jelly, liquid $C_6$-$C_{16}$ alkanes, polydecenes, liquid esters of fatty acids and/or of fatty alcohols other than triglycerides, and liquid fatty alcohols, or mixtures thereof, and even more preferentially from liquid petroleum jelly, liquid $C_6$-$C_{16}$ alkanes and polydecenes.

Even more preferentially, the liquid fatty substances are chosen from liquid petroleum jelly and octyldodecanol.

Obviously, the composition according to the invention may comprise one or more additional fatty substances other than the liquid fatty substances that have just been described, which are not liquid at room temperature and atmospheric pressure.

The composition according to the invention comprises at least 10% by weight of liquid fatty substance(s).

According to one embodiment, the composition according to the invention preferably comprises at least 20% by weight, better still at least 30% by weight, even better still at least 40% by weight and even more advantageously at least 45% by weight. The content of liquid fatty substance may range up to 90% by weight and better still up to 80% relative to the total weight of the composition.

b) Amphoteric Surfactants

The composition of the invention also comprises b) one or more surfactants chosen from the compounds of formula (I) below:

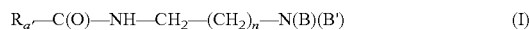

$$R_{a'}-C(O)-NH-CH_2-(CH_2)_n-N(B)(B') \qquad (I)$$

in which:

B represents the group $-CH_2-CH_2-O-X'$;
B' represents the group $-(CH_2)_zY'$, with z=1 or 2;
X' represents the group $-CH_2-C(O)OH$, $-CH_2-C(O)OZ'$, $-CH_2-CH_2-C(O)OH$ or $-CH_2-CH_2-C(O)OZ'$, or a hydrogen atom;
Y' represents the group $-C(O)OH$, $-C(O)OZ''$, $-CH_2-CH(OH)-SO_3H$ or the group $-CH_2-CH(OH)-SO_3-Z''$;
Z' and Z'' represent, independently of each other, a cationic counterion derived from an alkali metal or alkaline-earth metal, such as sodium, an ammonium ion or an ion derived from an organic amine;
$R_{a'}$ represents a $C_{10}$-$C_{30}$ alkyl or alkenyl group derived from an acid $R_{a'}-C(O)OH$, which is preferably present in copra oil or in hydrolysed linseed oil, an alkyl group, especially a $C_{17}$ group and its iso form, or an unsaturated $C_{17}$ group and
n represents an integer ranging from 1 to 10 and preferably from 1 to 5,
or quaternized forms thereof.

Use may be made especially of the compounds known under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid and cocoamphodipropionic acid. According to a preferred embodiment, B represents the group $-CH_2-CH_2-O-CH_2-C(O)OZ'$ and B' represents the group $-CH_2-C(O)OZ''$, Z' and Z'' having the same meaning as above.

Preferably, the compound of formula (I) is not quaternized.

Use is preferably made of disodium cocoamphodiacetate, for instance the product sold by the company Rhodia under the trade name Miranol® C2M Concentrate.

In the composition of the invention, the amount of amphoteric surfactant(s) of formula (I) in the composition preferably ranges from 0.1% to 20% by weight, better still from 0.5% to 10% by weight and even better still from 1% to 5% by weight relative to the total weight of the composition.

c) Nonionic Oxyethylenated Amide or Fatty Alcohol Surfactants

The composition according to the invention contains at least one nonionic surfactant chosen from oxyethylenated amide, oxyethylenated (OE) fatty alcohol comprising less than 10 OE units and mixture thereof.

The amount of nonionic surfactants(s) chosen from oxyethylenated amide and/or oxyethylenated (OE) fatty alcohol comprising less than 10 OE units preferably ranges from 0.01% to 20%, better still from 0.1% to 10%, preferably from 0.5% to 10% and preferably from 0.5% to 5% by weight relative to the total weight of the composition.

Oxyethylenated Amide Surfactant.

Preferably, the nonionic oxyethylenated amide is of formula (Ia)

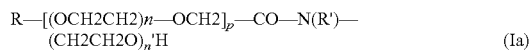
(Ia)

in which:
p denotes 0 or 1,
n denotes a number ranging from 1 to 10 and preferably from 1 to 6,
n' denotes a number ranging from 1 to 100 and preferably from 1 to 60,
R' denotes a hydrogen atom or a CH2CH2OH radical and preferably a hydrogen atom,
R denotes a C10-C30 and preferably C12-C22 alkyl or alkenyl radical.

Examples of compounds of formula (Ia) that may be mentioned include Amidet A15 sold by the company Kao (INCI name: Trideceth-2 carboxamide MEA), Ethomid HP 60 sold by the company Akzo Nobel (INCI name: PEG-50 Hydrogenated Palmamide) and Amidet N sold by the company Kao (INCI name: PEG-4 Rapeseedamide).

According to a particular embodiment, the nonionic oxyethylenated amide surfactant is rapeseed amide oxyethylenated with 4 oxyethylene units.

The amount of nonionic oxyethylenated amide surfactants(s) preferably ranges from 0.1% to 20%, better still from 0.5% to 10% and preferably from 1% to 5% by weight relative to the total weight of the composition.

Oxyethylenated Fatty Alcohol Comprising Less than 10 OE Units

The oxyethylenated fatty alcohols comprising less than 10 OE units may comprise from 1 to 9 OE units and are preferably chosen from oxyethylenated derivatives of saturated or unsaturated, linear or branched, preferably linear, $C_8$-$C_{30}$ and preferably $C_{12}$-$C_{22}$ fatty alcohols, for instance cetyl alcohol, oleyl alcohol, oleocetyl alcohol, lauryl alcohol, behenyl alcohol, cetearyl alcohol, stearyl alcohol and isostearyl alcohol, and mixtures thereof.

As oxyethylenated fatty alcohols comprising less than 10 OE units, use is preferably made of oxyethylenated fatty alcohols comprising from 2 to 8 and preferably from 2 to 6 OE units, for instance products of addition of ethylene oxide and lauryl alcohol, for instance lauryl alcohol 2 OE (CTFA name: laureth-2), products of addition of ethylene oxide and stearyl alcohol, for instance stearyl alcohol 2 OE (CTFA name: steareth-2), products of addition of ethylene oxide and decyl alcohol, for instance decyl alcohol 3 OE (CTFA name: deceth-3), decyl alcohol 5 OE (CTFA name: deceth-5), products of addition of ethylene oxide and oleocetyl alcohol, for instance oleocetyl alcohol 5 OE (CTFA name: oleoceteth-5), and mixtures thereof.

Even more preferentially oxyethylenated fatty alcohols that will be used are those comprising from 2 to 4 OE units and better still those comprising 2 OE units.

The content of oxyethylenated fatty alcohols comprising less than 10 OE units may range from 0.01% to 10% by weight, preferably from 0.1% to 5% by weight and better still from 0.5% to 2% by weight relative to the total weight of the composition.

According to an embodiment, the composition according to the invention contains at least one nonionic surfactant chosen from oxyethylenated amide and at least one nonionic surfactant chosen from oxyethylenated (OE) fatty alcohol comprising less than 10 OE units, that may be chosen among those described above.

Additional Surfactants

The composition for dyeing keratin fibres according to the invention may contain one or more additional or supplementary surfactants, i.e. other than the amphoteric surfactants of formula (I) and from the nonionic oxyethylenated amide or fatty alcohol with less than OE 10 units surfactants as defined previously. According to a particular embodiment of the invention, the additional surfactant(s) are chosen from anionic, cationic, nonionic and amphoteric surfactants, and preferentially nonionic surfactants.

The term "anionic surfactant" means a surfactant comprising, as ionic or ionizable groups, only anionic groups. These anionic groups are preferably chosen from the following groups:

—C(O)—OH, —C(O)—O$^-$, —SO$_3$H, —S(O)$_2$O$^-$, —OS(O)$_2$OH, —OS(O)$_2$O$^-$, —P(O)OH$_2$, —P(O)$_2$O, —P(O)O$_2$—, —P(OH)$_2$, =P(O)OH, —P(OH)O$^-$, =P(O)O$^-$, =POH, =PO$^-$; the anionic parts comprising a cationic counterion such as an alkali metal, an alkaline-earth metal or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, and in particular sodium or magnesium salts.

Among the anionic surfactants mentioned, use is preferably made of $(C_6-C_{24})$alkyl sulfates, $(C_6-C_{24})$alkyl ether sulfates comprising from 2 to 50 ethylene oxide units, especially in the form of alkali metal, ammonium, amino alcohol and alkaline-earth metal salts, or a mixture of these compounds.

In particular, it is preferred to use $(C_{12}-C_{20})$alkyl sulfates, $(C_{12}-C_{20})$alkyl ether sulfates comprising from 2 to 20 ethylene oxide units, especially in the form of alkali metal, ammonium, amino alcohol and alkaline-earth metal salts, or a mixture of these compounds. Better still, it is preferred to use sodium lauryl ether sulfate containing 2.2 mol of ethylene oxide.

According to one embodiment, the composition according to the invention comprises at least one additional surfactant chosen from anionic surfactants, in particular from $(C_6-C_{24})$ alkyl sulfates.

The cationic surfactant(s) that may be used in the composition according to the invention comprise, for example, optionally polyoxyalkylenated primary, secondary or tertiary fatty amine salts, quaternary ammonium salts, and mixtures thereof.

Examples of quaternary ammonium salts that may especially be mentioned include:
those corresponding to the general formula (A4) below:

in which formula (A4):
$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and
$X^-$ represents an organic or mineral anionic counterion, such as that chosen from halides, acetates, phosphates, nitrates, $(C_1-C_4)$alkyl sulfates, $(C_1-C_4)$alkylsulfonates or $(C_1-C_4)$alkylarylsulfonates, in particular methyl sulfate and ethyl sulfate.

The aliphatic groups of $R_8$ to $R_{11}$ may also comprise heteroatoms especially such as oxygen, nitrogen, sulfur and halogens.

The aliphatic groups of $R_8$ to $R_{11}$ are chosen, for example, from $C_1-C_{30}$ alkyl, $C_1-C_{30}$ alkoxy, polyoxy$(C_2-C_6)$alkylene, $C_1-C_{30}$ alkylamide, $(C_{12}-C_{22})$alkylamido$(C_2-C_6)$alkyl, $(C_{12}-C_{22})$alkyl acetate, and $C_1-C_{30}$ hydroxyalkyl groups; $X^-$ is an anionic counterion chosen from halides, phosphates, acetates, lactates, $(C_1-C_4)$alkyl sulfates, and $(C_1-C_4)$alkylsulfonates or $(C_1-C_4)$alkylarylsulfonates.

Among the quaternary ammonium salts of formula (A4), preference is given firstly to tetraalkylammonium chlorides, for instance dialkyldimethylammonium or alkyltrimethylammonium chlorides in which the alkyl group comprises approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (A5) below:

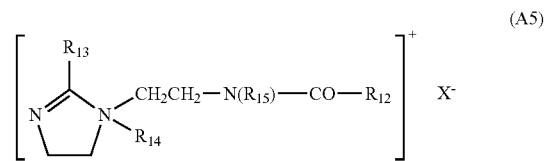

in which formula (A5):
$R_{12}$ represents an alkenyl or alkyl group comprising from 8 to 30 carbon atoms, for example fatty acid derivatives of tallow;
$R_{13}$ represents a hydrogen atom, a $C_1-C_4$ alkyl group or an alkenyl or alkyl group comprising from 8 to 30 carbon atoms;
$R_{14}$ represents a $C_1-C_4$ alkyl group;
$R_{15}$ represents a hydrogen atom or a $C_1-C_4$ alkyl group;
$X^-$ represents an organic or mineral anionic counterion, such as that chosen from halides, phosphates, acetates, lactates, $(C_1-C_4)$alkylsulfates, $(C_1-C_4)$alkylsulfonates or $(C_1-C_4)$alkylarylsulfonates.

Preferably, $R_{12}$ and $R_{13}$ denote a mixture of alkenyl or alkyl groups comprising from 12 to 21 carbon atoms, for example fatty acid derivatives of tallow, $R_{14}$ denotes a methyl group, and $R_{15}$ denotes a hydrogen atom. Such a product is sold, for example, under the name Rewoquat® W 75 by the company Rewo;

quaternary diammonium or triammonium salts, in particular of formula (A6) below:

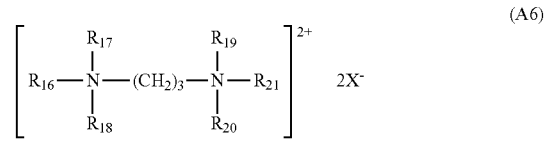

in which formula (A6):
$R_{16}$ denotes an alkyl group comprising approximately from 16 to 30 carbon atoms, which is optionally hydroxylated and/or interrupted with one or more oxygen atoms;
$R_{17}$ is chosen from hydrogen, an alkyl group comprising from 1 to 4 carbon atoms or a group $—(CH_2)_3—N^+$ $(R_{16a})(R_{17a})(R_{18a})$, $X^-$;
$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and
$X^-$, which may be identical or different, represent an organic or mineral anionic counterion, such as that chosen from halides, acetates, phosphates, nitrates, $(C_1-C_4)$alkylsulfates, $(C_1-C_4)$alkylsulfonates or $(C_1-C_4)$alkylarylsulfonates, more particularly methyl sulfate and ethyl sulfate.

Such compounds are, for example, Finquat CT-P, provided by the company Finetex (Quaternium 89), and Finquat CT, provided by the company Finetex (Quaternium 75);

quaternary ammonium salts containing one or more ester functions, such as those of formula (A7) below:

(A7)

$$R_{24}\underset{O}{\overset{O}{\parallel}}{-}{\left[{O}{-}{C}_{r}{H}_{r2}{(OH)}_{r1}\right]}_{y}{-}\overset{{(C}_{s}{H}_{2s})_{z}{-}R_{25}}{\underset{R_{22}}{\overset{X^{-}}{N^{+}}}}{-}{\left[{C}_{t}{H}_{t2}{(OH)}_{t1}{-}O\right]}_{x}{-}R_{23}$$

in which formula (A7):

$R_{22}$ is chosen from $C_1$-$C_6$ alkyl groups and $C_1$-$C_6$ hydroxyalkyl or $C_1$-$C_6$ dihydroxyalkyl groups;

$R_{23}$ is chosen from:
the group $$R_{26}\underset{}{\overset{O}{\underset{\parallel}{-C-}}},$$

linear or branched, saturated or unsaturated $C_1$-$C_{22}$ hydrocarbon-based groups $R_{27}$,
a hydrogen atom, $R_{25}$ is chosen from:
the group $$R_{28}\underset{}{\overset{O}{\underset{\parallel}{-C-}}},$$

linear or branched, saturated or unsaturated $C_1$-$C_6$ hydrocarbon-based groups $R_{29}$,
a hydrogen atom, $R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6, r1 and t1, which may be identical or different, are equal to 0 or 1, with r2+r1=2r and t1+t2=2t, y is an integer ranging from 1 to 10, x and z, which may be identical or different, are integers ranging from 0 to 10;

$X^-$ represents an organic or mineral anionic counterion, with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is an $R_{29}$ hydrocarbon-based group, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion $X^-$ is preferably a halide, such as chloride, bromide or iodide; a ($C_1$-$C_4$)alkyl sulfate or a ($C_1$-$C_4$)alkylsulfonate or ($C_1$-$C_4$)alkylarylsulfonate. However, it is possible to use methanesulfonate, phosphate, nitrate, tosylate, an anion derived from an organic acid, such as acetate or lactate, or any other anion that is compatible with the ammonium containing an ester function.

The anionic counterion $X^-$ is even more particularly chloride, methyl sulfate or ethyl sulfate.

Use is made more particularly, in the composition according to the invention, of the ammonium salts of formula (A7) in which:

$R_{22}$ denotes a methyl or ethyl group,
x and y are equal to 1,
z is equal to 0 or 1,
r, s and t are equal to 2,
$R_{23}$ is chosen from:
the group $$R_{26}\underset{}{\overset{O}{\underset{\parallel}{-C-}}}$$

methyl, ethyl or $C_{14}$-$C_{22}$ hydrocarbon-based groups,
a hydrogen atom,
$R_{25}$ is chosen from:
the group $$R_{28}\underset{}{\overset{O}{\underset{\parallel}{-C-}}}$$

a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based radicals are linear.

Among the compounds of formula (A7), examples that may be mentioned include salts, especially the chloride or methyl sulfate, of diacyloxyethyldimethylammonium, diacyloxyethylhydroxyethylmethylammonium, monoacyloxyethyldihydroxyethy-lmethyl-ammonium, triacyloxyethylmethylammonium or monoacyloxyethylhydroxyethyldimethyl-ammonium, and mixtures thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in patents U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylammonium salts, and mixtures thereof, and more particularly behenyltrimethylammonium chloride, cetyltrimethylammonium chloride and dipalmitoylethylhydroxyethylammonium methosulfate, and mixtures thereof.

Additional amphoteric surfactants that may especially be mentioned include betaines and in particular ($C_8$-$C_{20}$)alkylbetaines such as cocoyl betaine, sulfobetaines, ($C_8$-$C_{20}$) alkylsulfobetaines, ($C_8$-$C_{20}$)alkylamido($C_1$-$C_6$)alkylbetaines, such as cocamidopropylbetaine, and ($C_8$-$C_{20}$) alkylamido($C_1$-$C_6$)alkylsulfobetaines.

Examples of nonionic surfactants, other than the nonionic oxyethylenated amide surfactant, that may be used in the composition used according to the invention are described, for example, in the *Handbook of Surfactants* by M. R. Porter, published by Blackie & Son (Glasgow and London), 1991, pp. 116-178. They are especially chosen from alcohols, α-diols and ($C_1$-$C_{20}$)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 1 to 100, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, derivatives of N-alkyl glucamine and of N-acyl methylglucamine, aldobionamides and amine oxides.

The nonionic surfactants are chosen more particularly from mono- or polyoxyalkylenated or mono- or polyglycerolated nonionic surfactants. The oxyalkylene units are more particularly oxyethylene or oxypropylene units, or a combination thereof, preferably oxyethylene units, other than the oxyethylenated nonionic amide or fatty alcohol surfactants as defined previously.

Examples of oxyalkylenated nonionic surfactants that may be mentioned include:
oxyalkylenated ($C_8$-$C_{24}$)alkylphenols;
saturated or unsaturated, linear or branched, oxyalkylenated $C_8$-$C_{30}$ alcohols;
saturated or unsaturated, linear or branched, oxyalkylenated $C_8$-$C_{30}$ amides;
esters of saturated or unsaturated, linear or branched, $C_8$-$C_{30}$ acids and of polyethylene glycols;
polyoxyethylenated esters of saturated or unsaturated, linear or branched, $C_8$-$C_{30}$ acids and of sorbitol;
saturated or unsaturated, oxyethylenated plant oils;
condensates of ethylene oxide and/or of propylene oxide, inter alia, alone or as mixtures;
oxyethylenated and/or oxypropylenated silicones.

These oxyalkylenated nonionic surfactants may have a number of moles of ethylene oxide ranging from 1 to 100, preferably from 2 to 50 and preferably from 2 to 30.

Advantageously, the nonionic surfactants do not comprise any oxypropylene units.

In accordance with one preferred embodiment of the invention, the additional oxyalkylenated nonionic surfactants are chosen from oxyethylenated $C_8$-$C_{30}$ alcohols comprising from 1 to 100 mol of ethylene oxide; polyoxyethylenated esters of linear or branched, saturated or unsaturated $C_8$-$C_{30}$ acids and of sorbitol comprising from 1 to 100 mol of ethylene oxide.

According to one embodiment, the composition according to the invention comprises at least one oxyethylenated nonionic surfactant comprising more than 10 OE, in particular comprising from 10 to 50 OE units.

These oxyethylenated nonionic surfactants are preferably chosen from oxyethylenated derivatives of saturated or unsaturated, linear or branched, preferably linear, $C_8$-$C_{30}$ and preferably $C_{12}$-$C_{22}$ fatty alcohols, for instance cetyl alcohol, oleyl alcohol, oleocetyl alcohol, lauryl alcohol, behenyl alcohol, cetearyl alcohol, stearyl alcohol and isostearyl alcohol, and mixtures thereof.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to formula (A8) below:

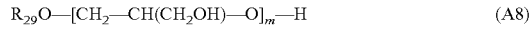

$$R_{29}O—[CH_2—CH(CH_2OH)—O]_m—H \qquad (A8)$$

in which formula (A8):
  $R_{29}$ represents a linear or branched $C_8$-$C_{40}$ and preferably $C_8$-$C_{30}$ alkyl or alkenyl radical; and
  m represents a number ranging from 1 to 30 and preferably from 1 to 10.

As examples of compounds of formula (A8) that are suitable within the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8$/$C_{10}$ alcohol containing 1 mol of glycerol, the $C_{10}$/$C_{12}$ alcohol containing 1 mol of glycerol and the $C_{12}$ alcohol containing 1.5 mol of glycerol.

Preferably, the additional surfactant(s) are chosen from nonionic surfactants and anionic surfactants, and mixtures thereof.

Preferably, the composition according to the invention comprises one or more additional surfactants preferably chosen from nonionic surfactants, in particular mono- or polyoxyethylenated nonionic surfactants other than the nonionic oxyethylenated amide and fatty alcohol with less than 10 OE units surfactant and the amphoteric surfactant of formula (I), and/or one or more anionic surfactants, in particular of the type such as ($C_6$-$C_{24}$)alkyl sulfates.

According to one variant of the invention, the composition according to the invention comprises:
  one or more surfactants chosen from oxyethylenated nonionic surfactants comprising more than 10 OE, in particular saturated or unsaturated, linear or branched, oxyethylenated $C_8$-$C_{30}$ fatty alcohols comprising more than 10 OE; and/or
  one or more anionic surfactants, in particular of the type such as ($C_6$-$C_{24}$)alkyl sulfates.

In the composition of the invention, the amount of additional surfactant(s) preferably ranges from 0.01% to 15% by weight, better still from 0.05% to 10% by weight and even better still from 0.1% to 5% by weight relative to the total weight of the composition.

d) Oxidation Dye Precursor

As indicated previously, the dye composition according to the invention comprises at least one oxidation dye precursor.

As oxidation dye precursors, use may be made of oxidation bases and couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(3-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof, described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl) methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 2-(3-aminopyrazolo[1,5-a]pyridin-2-yloxy)ethanol, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof. Salts of 2-(3-aminopyrazolo[1,5-a]pyridin-2-yloxy)ethanol are particularly appreciated.

Among the pyrimidine derivatives, mention may be made of the compounds described, for example, in patents DE 2359399, JP 88-169571, JP 05-63124 and EP 0 770 375 or patent application WO 96/15765, such as 2,4,5,6-tetraamino-pyrimidine, 4-hydroxy-2,5,6-triamino-pyrimidine, 2-hydroxy-4,5,6-triamino-pyrimidine, 2,4-dihydroxy-5,6-diamino-pyrimidine, 2,5,6-triamino-pyrimidine and the addition salts thereof, and the tautomeric forms thereof, when a tautomeric equilibrium exists.

Among the pyrazole derivatives, examples that may be mentioned include 3,4-diaminopyrazole, 4-amino-1,3-dimethyl-5-hydrazinopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

Among the couplers that may be used in the composition according to the invention, mention may be made especially of meta-phenylenediamines, meta-aminophenols, meta-diphenols, naphthalene-based couplers, heterocyclic couplers, for instance indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines, and the addition salts of these compounds with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, the addition salts thereof with an acid, and mixtures thereof.

The addition salts of the oxidation bases and couplers are especially chosen from the addition salts with an acid such as the hydrochlorides, hydrobromides, sulfates, citrates, succinates, tartrates, lactates, tosylates, benzenesulfonates, phosphates and acetates.

The oxidation base(s) are each generally present in an amount of from 0.0001% to 10% by weight relative to the total weight of the composition of the invention, and preferably from 0.005% to 5% by weight relative to the total weight of the composition.

The coupler(s) each generally represent from 0.0001% to 10% by weight relative to the total weight of the composition, and preferably from 0.005% to 5% by weight relative to the total weight of the composition of the invention.

Additional Dyes

The composition of the invention may also comprise one or more direct dyes. The latter dyes are more particularly chosen from ionic or nonionic species, preferably cationic or nonionic species. These direct dyes may be synthetic or of natural origin.

Examples of suitable direct dyes that may be mentioned include azo direct dyes; methine direct dyes; carbonyl direct dyes; azine direct dyes; nitro(hetero)aryl direct dyes; tri(hetero)arylmethane direct dyes; porphyrin direct dyes; phthalocyanine direct dyes, and natural direct dyes, alone or as mixtures.

More particularly, the azo dyes comprise an —N=N— function, the two nitrogen atoms of which are not simultaneously engaged in a ring. However, it is not excluded for one of the two nitrogen atoms of the sequence —N=N— to be engaged in a ring.

The dyes of the methine family are more particularly compounds comprising at least one sequence chosen from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of the type such as methines, azomethines, monoarylmethanes and diarylmethanes, indoamines (or diphenylamines), indophenols, indoanilines, carbocyanines, azacarbocyanines and isomers thereof, diazacarbocyanines and isomers thereof, tetraazacarbocyanines and hemicyanines.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro(hetero)aromatic dyes are more particularly nitrobenzene or nitropyridine direct dyes.

As regards the dyes of porphyrin or phthalocyanine type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitrobenzene dyes; azo direct dyes; azomethine direct dyes; methine direct dyes; azacarbocyanines, for instance tetraazacarbocyanines (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures.

Among the natural dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin, haematin, haematoxylin, brasilin, brasilein and orceins. Use may also be made of extracts or decoctions comprising these natural dyes and especially henna-based poultices or extracts.

When they are present, the direct dye(s) more particularly represent from 0.0001% to 10% by weight and preferably from 0.005% to 5% by weight relative to the total weight of the composition.

e) Chemical Oxidizing Agent

The composition of the invention comprises e) one or more chemical oxidizing agents. The term "chemical oxidizing agent" means an oxidizing agent other than atmospheric oxygen. The composition of the invention preferentially contains one or more chemical oxidizing agents.

More particularly, the chemical oxidizing agent(s) are chosen from hydrogen peroxide, urea peroxide, alkali metal bromates, peroxygenated salts, for instance persulfates or perborates, peracids and precursors thereof and alkali metal or alkaline-earth metal percarbonates.

Advantageously, this oxidizing agent is hydrogen peroxide.

The concentration of chemical oxidizing agents may range more particularly from 0.1% to 50% by weight, even more preferentially from 0.5% to 20% by weight and better still from 1% to 15% by weight relative to the weight of the composition.

Preferably, the composition of the invention does not contain any peroxygenated salts.

Basifying Agents:

The composition of the invention may also comprise one or more basifying agents. According to one embodiment of the invention, the composition and the process for treating keratin fibres use one or more basifying agents. The basifying agent(s) may be mineral or organic or hybrid.

The mineral basifying agent(s) are preferably chosen from aqueous ammonia, alkali metal carbonates or bicarbonates such as sodium carbonate or bicarbonate, potassium carbonate or bicarbonate, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chains comprising more than ten carbon atoms.

The organic basifying agent(s) are chosen, for example, from alkanolamines, oxyethylenated and/or oxypropylenated ethylenediamines, amino acids and the compounds of formula (II) below:

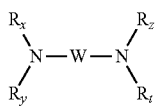
(II)

in which formula (II) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (II) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

The organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function more particularly chosen from carboxylic acid, sulfonic acid, phosphonic acid and phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (III) below:

(III)

in which formula (III) R represents a group chosen from: imidazolyl, preferably 4-imidazolyl; —$(CH_2)_3NH_2$; —$(CH_2)_2NH_2$; —$(CH_2)_2$—NH—C(O)—$NH_2$; and

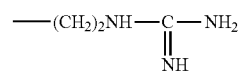

The compounds corresponding to formula (III) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the basifying agent(s) present in the composition of the invention are chosen from alkanolamines, amino acids in neutral or ionic form, in particular basic amino acids, and preferably corresponding to those having the formula (III). Even more preferentially, the basifying agent(s) are chosen from monoethanolamine (MEA) and basic amino acids in neutral or ionic form.

Advantageously, the composition according to the invention has a content of basifying agent(s) ranging from 0.01% to 30% by weight and preferably from 0.1% to 20% by weight relative to the weight of the composition.

According to a first particular embodiment, the composition does not contain any aqueous ammonia, or a salt thereof, or else the process according to the invention does not use aqueous ammonia, or a salt thereof, as basifying agent.

If, however, according to another particular embodiment, the composition or the process did use any, its content would advantageously not exceed 0.03% by weight (expressed as $NH_3$) and would preferably not exceed 0.01% by weight relative to the weight of the composition of the invention. Preferably, if the composition comprises aqueous ammonia, or a salt thereof, then the amount of basifying agent(s) other than the aqueous ammonia is greater than that of the aqueous ammonia (expressed as $NH_3$).

Solvent

The composition according to the invention may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The organic solvent(s), if they are present, represent a content usually ranging from 1% to 40% by weight and preferably from 5% to 30% by weight relative to the weight of the composition.

Other Additives

The composition according to the invention may also contain various adjuvants conventionally used in hair dye compositions, such as anionic, cationic, nonionic, amphoteric or zwitterionic polymers or mixtures thereof; mineral thickeners, and in particular fillers such as clays or talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of the composition.

The composition may especially comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The fumed silicas may be obtained by high-temperature hydrolysis of a volatile silicon compound in an oxyhydrogen flame, producing a finely divided silica. This process makes it possible especially to obtain hydrophilic silicas bearing a large number of silanol groups at their surface. Such hydrophilic silicas are sold, for example, under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of the silica via chemical reaction in order to reduce the number of silanol groups. It is possible especially to replace silanol groups with hydrophobic groups: a hydrophobic silica is then obtained.

The hydrophobic groups may be:
trimethylsiloxyl groups, which are obtained especially by treating fumed silica in the presence of hexamethyldisilazane. Silicas thus treated are known as "Silica silylate" according to the CTFA (6th Edition, 1995). They are sold, for example, under the references Aerosil R812® by the company Degussa and Cab-O-Sil TS-530® by the company Cabot.
dimethylsilyloxyl or polydimethylsiloxane groups, which are obtained especially by treating fumed silica in the presence of polydimethylsiloxane or dimethyldichlorosilane. Silicas thus treated are known as "Silica dimethyl silylate" according to the CTFA (6th Edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

When it is present, the mineral thickener represents from 1% to 30% by weight relative to the weight of the composition.

The composition may also comprise one or more organic thickeners.

These thickeners may be chosen from polymeric thickeners such as cellulose-based thickeners (hydroxyethylcellulose, hydroxypropylcellulose or carboxymethylcellulose), guar gum and derivatives thereof, in particular nonionic guar gums modified with $C_1$-$C_6$ hydroxyalkyl groups, gums of microbial origin (xanthan gum, scleroglucan gum), crosslinked acrylic acid or acrylamidopropanesulfonic acid (AMPS®) homopolymers, crosslinked or non-crosslinked acrylamidopropanesulfonic acid copolymers and associative polymers (polymers comprising hydrophilic regions and fatty-chain hydrophobic regions (alkyl or alkenyl comprising at least 10 carbon atoms) that are capable, in an aqueous medium, of reversibly combining with each other or with other molecules).

According to a particular embodiment, the composition comprises at least one thickener chosen from nonionic guar gums modified with $C_1$-$C_6$ hydroxyalkyl groups, crosslinked or non-crosslinked, neutralized or non-neutralized copolymers of AMPS®, in particular copolymers of AMPS® and of hydroxylated $C_2$-$C_4$ alkyl (meth)acrylate, and mixtures thereof.

The content of organic thickener(s), if they are present, usually ranges from 0.01% to 20% by weight and preferably from 0.1% to 5% by weight relative to the weight of the composition.

According to a preferred embodiment, the composition comprises at least one cationic polymer preferably chosen from homopolymers of dimethyldiallylammonium salts (for example chloride), and polymers consisting of repeating units corresponding to the formula:

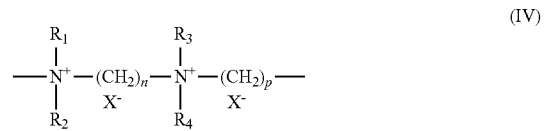

(IV)

in which R1, R2, R3 and R4, which may be identical or different, denote an alkyl or hydroxyalkyl radical containing from 1 to 4 carbon atoms approximately, n and p are integers ranging from 2 to 20 approximately, and X⁻ is an anion derived from a mineral or organic acid.

A particularly preferred compound of formula (IV) is that for which R1, R2, R3 and R4 represent a methyl radical and n=3, p=6 and X=Cl, known as Hexadimethrine chloride according to the INCI (CTFA) nomenclature.

The solids content of cationic polymers, if they are present, usually ranges from 0.01% to 20% by weight and preferably from 0.05% to 5% by weight, relative to the weight of the composition.

The composition of the invention may be in various forms, for instance a solution, an emulsion (milk or cream) or a gel, preferably in the form of an emulsion and particularly of a direct emulsion.

Process of the Invention

The composition according to the invention comprising ingredients a) to e) as defined previously is applied to dry or wet keratin fibres. It is left in place on the fibres for a time generally of from 1 minute to 1 hour and preferably from 5 minutes to 30 minutes.

The temperature during the dyeing process is conventionally between room temperature (between 15° C. and 25° C.) and 80° C. and preferably between room temperature and 60° C.

After the treatment, the human keratin fibres are optionally rinsed with water, optionally washed with a shampoo and then rinsed with water, before being dried or left to dry.

The composition according to the invention is generally prepared by mixing at least two compositions.

In particular, the composition according to the invention comprising ingredients a) to e) as defined previously results from the mixing of two compositions:
- a composition (A) comprising one or more oxidation dye precursors and
- a composition (B) comprising one or more chemical oxidizing agents, it being understood that:
at least one of the compositions (A) and (B) comprises:
  at least one liquid fatty substance as defined previously;
  at least one amphoteric surfactant of formula (I) below:

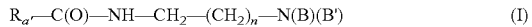

in which:
B represents the group —CH₂—CH₂—O—X';
B' represents the group —(CH₂)_zY', with z=1 or 2;
X' represents the group —CH₂—C(O)OH, —CH₂—C(O)OZ', —CH₂—CH₂—C(O)OH or —CH₂—CH₂—C(O)OZ', or a hydrogen atom;
Y' represents the group —C(O)OH, —C(O)OZ", —CH₂—CH(OH)—SO₃H or the group —CH₂—CH(OH)—SO₃—Z";
Z' and Z" represent, independently of each other, a cationic counterion derived from an alkali metal or alkaline-earth metal, such as sodium, an ammonium ion or an ion derived from an organic amine;
R_a' represents a C₁₀-C₃₀ alkyl or alkenyl group derived from an acid R_a'—C(O)OH, which is preferably present in copra oil or in hydrolysed linseed oil, an alkyl group, especially a C₁₇ group and its iso form, or an unsaturated C₁₇ group and
n represents an integer ranging from 1 to 10 and preferably from 1 to 5, and at least one nonionic surfactant chosen from oxyethylenated amide, oxyethylenated (OE) fatty alcohol comprising less than 10 OE units and mixture thereof, the amount of liquid fatty substances in compositions (A) and/or (B) being such that the liquid fatty substances represent at least 10% by weight of, relative to the total weight of the composition resulting from the mixing.

Preferably, composition (A) comprises at least one liquid fatty substance, preferably in a content of at least 10% by weight, preferably at least 20% by weight, better still at least 30% by weight, even better still at least 40% by weight and even more advantageously at least 50% by weight of liquid fatty substance(s) relative to the total weight of composition (A).

Preferably, composition (A) and composition (B) each comprise at least one liquid fatty substance, preferably in a content of at least 10% by weight, preferably at least 20% by weight, better still at least 30% by weight, even better still at least 40% by weight and even more advantageously at least 50% by weight of liquid fatty substance(s) relative to the total weight of each composition (A) and (B).

According to one embodiment, the amphoteric surfactant as described above is present in composition (A) and the nonionic surfactants chosen from oxyethylenated amide, oxyethylenated (OE) fatty alcohol comprising less than 10 OE units is present in composition (B).

Preferentially, at least one of the compositions (A) or (B) is aqueous.

Preferably, composition (A) is aqueous.

Even more preferentially, both the compositions (A) and (B) are aqueous.

The term "aqueous composition" means a composition comprising at least 5% water. Preferably, an aqueous composition comprises more than 10% by weight of water and more advantageously still more than 20% by weight of water.

In this variant, composition (A) comprises at least 50% of fatty substances and even more preferentially at least 50% of non-silicone fatty substances that are liquid at room temperature (25° C.).

Preferably, composition (A) is a direct or inverse emulsion and preferably a direct (O/W) emulsion.

In this variant, compositions (A) and (B) are preferably mixed in a weight ratio (A)/(B) ranging from 0.2 to 10 and better still from 0.5 to 2.

Finally, the invention relates to a multi-compartment device comprising a first compartment containing composition (A) as described above and at least a second compartment containing composition (B) as described above, the compositions of the compartments being intended to be mixed before application to give the composition after mixing according to the invention.

The examples that follow serve to illustrate the invention without, however, being limiting in nature.

EXAMPLE 1

The following compositions are prepared (unless otherwise mentioned, the amounts are expressed in g % of product per se):

Composition (A)

| | |
|---|---|
| Monoethanolamine | 4.35 |
| Polydimethyldiallylammonium chloride (non-stabilized aqueous 33% solution, Polyquaternium-6) (Merquat 106 from Nalco) | 1.2 AM |

-continued

| | |
|---|---|
| Hydroxypropyl guar (Jaguar HP 105 from Rhodia Chimie) | 0.8 |
| 2,5-Toluenediamine | 0.346 |
| PEG-40 hydrogenated castor oil | 1 |
| Hexadimethrine chloride | 0.6 AM |
| Disodium cocoamphodiacetate (Miranol C2M Conc. NP from Rhodia) | 1.89 AM |
| Sodium lauryl sulfate | 1.1 |
| Sodium metabisulfite | 0.22 |
| Resorcinol | 0.342 |
| m-Aminophenol | 0.038 |
| Liquid petroleum jelly | 60 |
| EDTA | 0.2 |
| Ascorbic acid | 0.12 |
| Water | qs 100 |

Composition (B)

| | |
|---|---|
| Hydrogen peroxide (aqueous 50% solution) | 6 AM |
| Tetrasodium pyrophosphate | 0.03 |
| Liquid petroleum jelly | 20 |
| Pentasodium pentetate | 0.06 |
| Polyquaternium-6 | 0.2 AM |
| Glycerol | 0.5 |
| Oxyethylenated (20 OE) stearyl alcohol (Brij S20-SO from Croda) | 5 |
| Cetearyl alcohol | 6 |
| Hexadimethrine chloride | 0.15 AM |
| PEG-4 rapeseedamide (Amidet N from Kao) | 1.19 |
| Phosphoric acid | qs pH 2.2 |
| Sodium stannate | 0.04 |
| Tocopherol | 0.1 |
| Water | qs 100 |

Compositions (A) and (B) are mixed at the time of use in the following proportions: 10 g of composition A and 10 g of composition B.

The resulting mixture is then applied to locks of grey hair containing 90% white hairs, in a proportion of 10 g of mixture per 1 g of hair.

The mixture is left in at room temperature for 30 minutes.

The hair is then rinsed, washed with a standard shampoo and dried.

Dark blonde locks (visual evaluation), whose coloration is powerful (good coloration build-up) and uniform, are obtained.

EXAMPLE 2

The following compositions are prepared (unless otherwise mentioned, the amounts are expressed in g % of product per se):

Composition (A')

| | |
|---|---|
| Monoethanolamine | 4.35 |
| Polydimethyldiallylammonium chloride (non-stabilized aqueous 33% solution, Polyquaternium-6) (Merquat 106 from Nalco) | 1.2 AM |
| Hydroxypropyl guar (Jaguar HP 105 from Rhodia Chimie) | 0.8 |
| 2,5-Toluenediamine | 0.346 |
| PEG-40 hydrogenated castor oil | 1 |
| Hexadimethrine chloride | 0.6 AM |
| Disodium cocoamphodiacetate (Miranol C2M Conc. NP from Rhodia) | 1.89 AM |
| Sodium lauryl sulfate | 1.1 |
| Sodium metabisulfite | 0.22 |
| Resorcinol | 0.342 |
| m-Aminophenol | 0.038 |
| Liquid petroleum jelly | 60 |
| EDTA | 0.2 |
| Ascorbic acid | 0.12 |
| Water | qs 100 |

Composition (B')

| | |
|---|---|
| Hydrogen peroxide (aqueous 50% solution) | 12 AM |
| Tetrasodium etidronate | 0.06 |
| Tetrasodium pyrophosphate | 0.04 |
| Liquid petroleum jelly | 50 |
| Sodium salicylate | 0.035 |
| Sorbitan isostearate | 0.011 |
| Oxyethylenated (2 OE) stearyl alcohol (Brij S2-SO from Croda) | 1.5 |
| Oxyethylenated (20 OE) stearyl alcohol (Brij S20-SO from Croda) | 1.5 |
| Polysorbate 60 | 0.011 |
| Ceteareth-60 myristyl alcohol | 0.2 |
| Sodium acrylamido-2-methylpropanesulfonate/hydroxyethyl acrylate copolymer (Sepinov EMT 10 from SEPPIC) | 0.4 AM |
| Phosphoric acid | qs pH 2.2 |
| Water | qs 100 |

Compositions (A') and (B') are mixed at the time of use in the following proportions: 10 g of composition A' and 10 g of composition B'.

The resulting mixture is then applied to locks of grey hair containing 90% white hairs, in a proportion of 10 g of mixture per 1 g of hair.

The mixture is left in at room temperature for 30 minutes.

The hair is then rinsed, washed with a standard shampoo and dried.

Dark blonde locks (visual evaluation), whose coloration is powerful (good coloration build-up) and uniform, are obtained.

The invention claimed is:

1. A cosmetic composition comprising:
   a) at least one liquid fatty substance, present in an amount of at least about 30% by weight, relative to the total weight of the composition;
   b) at least one amphoteric surfactant of formula (I) below:

$$R_a\text{—C(O)—NH—CH}_2\text{—(CH}_2)_n\text{—N(B)(B')} \qquad (I)$$

wherein:
   B represents the group —$CH_2$—$CH_2$—O—X';
   B' represents the group —$(CH_2)_z$Y', wherein z is equal to 1 or 2;
   X' is chosen from —$CH_2$—C(O)OH, —$CH_2$—C(O)OZ', —$CH_2$—$CH_2$—C(O)OH, —$CH_2$—$CH_2$—C(O)OZ', or a hydrogen atom;
   Y' is chosen from —C(O)OH, —C(O)OZ'', —$CH_2$—CH(OH)—$SO_3$H, or $CH_2$—CH(OH)—$SO_3$—Z'';
   Z' and Z'', independently of each other, are chosen from a cationic counterion derived from an alkali metal or alkaline-earth metal, an ammonium ion, or an ion derived from an organic amine;
   $R_{a'}$ is chosen from a $C_{10}$-$C_{30}$ alkyl or alkenyl group derived from an acid $R_{a'}$—C(O)OH, an alkyl group, or an unsaturated $C_{17}$ group; and
   n is an integer ranging from 1 to 10,
   or quaternized forms thereof;
   c) at least one nonionic surfactant chosen from oxyethylenated amide, oxyethylenated fatty alcohol comprising less than 10 OE units, or mixtures thereof;
   d) at least one oxidation dye precursor; and
   e) at least one chemical oxidizing agent.

2. The composition according to claim 1, wherein B represents the group —CH$_2$—CH$_2$—O—CH$_2$—C(O)OZ' and B' represents the group —CH$_2$—C(O)OZ".

3. The composition according to claim 1, wherein the at least one amphoteric surfactant of formula (I) is chosen from disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid, or mixtures thereof.

4. The composition according to claim 1, wherein the at least one amphoteric surfactant of formula (I) is present in amount ranging from about 0.1% to about 20% by weight, relative to the total weight of the composition.

5. The composition according to claim 1, wherein the at least one nonionic surfactant chosen from oxyethylenated amide is chosen from the compounds of formula (Ia) below:

R—[(OCH$_2$CH$_2$)$_n$—OCH$_2$]$_p$—CO—N(R')—(CH$_2$CH$_2$O)$_{n'}$H     (Ia)

wherein:
p is equal to 0 or 1,
n is a number ranging from 1 to 10,
n' is a number ranging from 1 to 100,
R' is chosen from a hydrogen atom or a CH$_2$CH$_2$OH radical, and
R is chosen from a C$_{10}$-C$_{30}$ or alkenyl radical.

6. The composition according to claim 1, wherein the at least one nonionic surfactant chosen from oxyethylenated amide is rapeseed acid amide oxyethylenated with 4 oxyethylene units.

7. The composition according to claim 1, wherein the at least one nonionic surfactant chosen from oxyethylenated fatty alcohols is chosen from oxyethylenated derivatives of saturated or unsaturated, linear or branched, C$_8$-C$_{30}$ fatty alcohols, or mixtures thereof.

8. The composition according to claim 1, wherein the at least one nonionic surfactant chosen from oxyethylenated fatty alcohols is chosen from oxyethylenated fatty alcohols comprising from 2 to 8 OE units.

9. The composition according to claim 1, wherein the at least one nonionic surfactant chosen from oxyethylenated fatty alcohols is chosen from the products of addition of ethylene oxide and lauryl alcohol, products of addition of ethylene oxide and stearyl alcohol, products of addition of ethylene oxide and decyl alcohol, products of addition of ethylene oxide and oleocetyl alcohol, or mixtures thereof.

10. The composition according to claim 1, wherein the at least one nonionic surfactant chosen from oxyethylenated fatty alcohols is chosen from oxyethylenated nonionic surfactants comprising 2 OE units.

11. The composition according to claim 1, wherein the at least one nonionic surfactant is present in an amount ranging from about 0.01% to about 20% by weight, relative to the total weight of the composition.

12. The composition according to claim 1, further comprising at least one surfactant chosen from nonionic surfactants, and/or at least one anionic surfactant.

13. The composition according to claim 1, further comprising at least one basifying agent chosen from aqueous ammonia, alkali metal carbonates or bicarbonates, sodium carbonate or bicarbonate, potassium carbonate or bicarbonate, sodium hydroxide or potassium hydroxide, organic amines chosen from alkanolamines, oxyethylenated and/or oxypropylenated ethylenediamines, amino acids, compounds of formula (II), or mixtures thereof:

wherein:
W is a divalent C$_1$-C$_6$ alkylene radical optionally substituted with at least one hydroxyl group or a C$_1$-C$_6$ alkyl radical, and/or optionally interrupted with at least one or heteroatom; and
R$_x$, R$_y$, R$_z$, R$_t$ and R$_u$, which may be identical or different, are chosen from a hydrogen atom, C$_1$-C$_6$ alkyl, C$_1$-C$_6$ hydroxyalkyl or C$_1$-C$_6$ aminoalkyl radical.

14. The composition according to claim 1, wherein the at least one chemical oxidizing agent is chosen from hydrogen peroxide, urea peroxide, alkali metal bromates, peroxygenated salts, persulfates, perborates, peracids or precursors thereof, or alkali metal or alkaline-earth metal percarbonates.

15. A process for dyeing keratin fibers, comprising applying to the keratin fibers, a composition comprising:
a) at least one liquid fatty substance, present in an amount of at least about 30% by weight, relative to the total weight of the composition;
b) at least one amphoteric surfactant of formula (I) below:

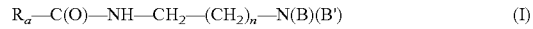

wherein:
B represents the group —CH$_2$—CH$_2$—O—X';
B' represents the group —(CH$_2$)$_z$Y', wherein z is equal to 1 or 2;
X' is chosen from —CH$_2$—C(O)OH, —CH$_2$—C(O)OZ', —CH$_2$—CH$_2$—C(O)OH, —CH$_2$—CH$_2$—C(O)OZ', or a hydrogen atom;
Y' is chosen from —C(O)OH, —C(O)OZ", —CH$_2$—CH(OH)—SO$_3$H, or CH$_2$—CH(OH)—SO$_3$—Z";
Z' and Z", independently of each other, are chosen from a cationic counterion derived from an alkali metal or alkaline-earth metal, an ammonium ion, or an ion derived from an organic amine;
R$_{a'}$ is chosen from a C$_{10}$-C$_{30}$ alkyl or alkenyl group derived from an acid R$_a$—C(O)OH, an alkyl group, or an unsaturated C$_{17}$ group; and
n is an integer ranging from 1 to 10,
or quaternized forms thereof;
c) at least one nonionic surfactant chosen from oxyethylenated amide, oxyethylenated fatty alcohol comprising less than 10 OE units, or mixtures thereof;
d) at least one oxidation dye precursor; and
e) at least one chemical oxidizing agent.

16. A multi-compartment device comprising:
a first compartment containing a first composition comprising at least one oxidation dye precursor; and
a second compartment containing a second composition comprising at least one chemical oxidizing agent,
wherein at least one of the first composition or second composition comprises:
at least one liquid fatty substance;
at least one amphoteric surfactant of formula (I) below:

wherein:
B represents the group —$CH_2$—$CH_2$—O—X';
B' represents the group —$(CH_2)_z$Y', wherein z is equal to 1 or 2;
X' is chosen from —$CH_2$—C(O)OH, —$CH_2$—C(O)OZ', —$CH_2$—$CH_2$—C(O)OH, —$CH_2$—$CH_2$—C(O)OZ', or a hydrogen atom;
Y' is chosen from —C(O)OH, —C(O)OZ", —$CH_2$—CH(OH)—$SO_3$H, or $CH_2$—CH(OH)—$SO_3$—Z";
Z' and Z", independently of each other, are chosen from a cationic counterion derived from an alkali metal or alkaline-earth metal, an ammonium ion, or an ion derived from an organic amine;
$R_{a'}$ is chosen from a $C_{10}$-$C_{30}$ alkyl or alkenyl group derived from an acid $R_{a'}$—C(O)OH, an alkyl group, or an unsaturated $C_{17}$ group; and
n is an integer ranging from 1 to 10,
or quaternized forms thereof; and
at least one nonionic surfactant chosen from oxyethylenated amide, oxyethylenated fatty alcohol comprising less than 10 OE units, or mixtures thereof;
further wherein the first composition and second composition are mixed before application to keratin fibers, and
the liquid fatty substance in the first composition and/or second composition being present in an amount of at least about 30% by weight, relative to the total weight of the composition after the first composition and the second composition are mixed.

17. The composition according to claim 1, wherein the at least one liquid fatty substance is chosen from liquid $C_6$-$C_{16}$ alkanes, liquid hydrocarbons comprising more than 16 carbon atoms, plant oils of triglyceride type, liquid synthetic triglycerides, liquid fatty alcohols, liquid fatty acid and/or fatty alcohol esters other than triglycerides, or mixtures thereof.

18. The composition according to claim 1, wherein the at least one liquid fatty substance is chosen from liquid petroleum jelly, liquid $C_6$-$C_{16}$ alkanes, polydecenes, liquid esters of fatty acids and/or of fatty alcohols other than triglycerides, liquid fatty alcohols, or mixtures thereof.

* * * * *

UNITED STATES PATENT AND TRADEMARK OFFICE
CERTIFICATE OF CORRECTION

| | |
|---|---|
| PATENT NO. | : 10,098,825 B2 |
| APPLICATION NO. | : 14/905574 |
| DATED | : October 16, 2018 |
| INVENTOR(S) | : Delphine Charrier et al. |

It is certified that error appears in the above-identified patent and that said Letters Patent is hereby corrected as shown below:

On the Title Page

Title (54), after "THEREOF" insert -- DYE COMPOSITION COMPRISING A PARTICULAR AMPHOTERIC SURFACTANT AND AN OXYETHYLENATED AMID SURFACTANT --.

In the Claims

Column 28, Line 44, please change "Ra" in the formula to -- Ra' --.

Column 30, Line 33, please change "Ra" in the formula to -- Ra' --.

Column 30, Line 48, please change "Ra" in the formula to -- Ra' --.

Signed and Sealed this
Sixteenth Day of April, 2019

Andrei Iancu
*Director of the United States Patent and Trademark Office*